(12) United States Patent
Park et al.

(10) Patent No.: US 10,940,036 B2
(45) Date of Patent: Mar. 9, 2021

(54) BALLOON CATHETER

(71) Applicant: Cryotherapeutics GmbH, Cologne (DE)

(72) Inventors: Peter Kyone Park, Milpitas, CA (US); Dominic Santoianni, Kirkland (CA); Stewart Maddison Fox, Cambridgeshire (GB); Peter Georg Laitenberger, Cambridgeshire (GB)

(73) Assignee: Cryotherapeutics GmbH, Cologne (DE)

( * ) Notice: Subject to any disclaimer, the term of this patent is extended or adjusted under 35 U.S.C. 154(b) by 166 days.

(21) Appl. No.: 16/300,602

(22) PCT Filed: May 9, 2017

(86) PCT No.: PCT/EP2017/061090
§ 371 (c)(1),
(2) Date: Nov. 12, 2018

(87) PCT Pub. No.: WO2017/194557
PCT Pub. Date: Nov. 16, 2017

(65) Prior Publication Data
US 2019/0209368 A1   Jul. 11, 2019

Related U.S. Application Data

(60) Provisional application No. 62/335,885, filed on May 13, 2016.

(51) Int. Cl.
*A61B 18/02*   (2006.01)
*A61F 7/12*   (2006.01)
(Continued)

(52) U.S. Cl.
CPC .............. *A61F 7/123* (2013.01); *A61B 18/02* (2013.01); *A61F 7/0085* (2013.01);
(Continued)

(58) Field of Classification Search
CPC ...... A61F 2007/0058; A61F 2007/0092; A61F 2007/126; A61F 7/0085; A61F 7/123;
(Continued)

(56) References Cited

U.S. PATENT DOCUMENTS 6,428,534 B1   8/2002   Joye et al.
2015/0238243 A1*  8/2015  Ingle .................... A61B 18/02
606/23

FOREIGN PATENT DOCUMENTS

EP          1428478       6/2004
WO     WO 2012/019156    2/2012
(Continued)

OTHER PUBLICATIONS

International Searching Authority—EPO, International Search Report and Written Opinion, PCT/EP2017/061090; dated Jul. 12, 2017. 10 pages.

*Primary Examiner* — Michael F Peffley
(74) *Attorney, Agent, or Firm* — Sunstein LLP

(57) ABSTRACT

A catheter is provided comprising a flexible heat transfer element provided on an outer surface of the catheter, a conduit arranged to supply an inflation fluid for inflating the flexible heat transfer element so as to form an inflated balloon, a guide wire lumen for receiving a guide wire, and an elongate cooling element arranged to cool said inflation fluid for inflating the balloon. Said cooling element and said guide wire lumen are arranged inside the flexible heat transfer element such that, when inflated the cooling element is substantially central within the balloon and said guide wire lumen is parallel to and radially offset from the cooling element.

20 Claims, 3 Drawing Sheets

(51) Int. Cl.
*A61F 7/00* (2006.01)
*A61B 18/00* (2006.01)
*A61M 25/10* (2013.01)

(52) U.S. Cl.
CPC .............. *A61B 2018/00011* (2013.01); *A61B 2018/0022* (2013.01); *A61B 2018/00023* (2013.01); *A61B 2018/00041* (2013.01); *A61B 2018/00577* (2013.01); *A61B 2018/0212* (2013.01); *A61B 2018/0268* (2013.01); *A61F 2007/0058* (2013.01); *A61F 2007/0092* (2013.01); *A61F 2007/126* (2013.01); *A61M 25/1002* (2013.01); *A61M 2025/1088* (2013.01)

(58) Field of Classification Search
CPC .......... A61B 18/02; A61B 2018/00011; A61B 2018/00023; A61B 2018/00041; A61B 2018/0022; A61B 2018/00577; A61B 2018/0212; A61B 2018/0268; A61M 2025/1088; A61M 25/1002
See application file for complete search history.

(56) References Cited

FOREIGN PATENT DOCUMENTS

WO    WO 2015/067414    5/2015
WO    WO-2015067414 A1 *    5/2015    ............. A61B 18/02

* cited by examiner

BALLOON CATHETER

CROSS-REFERENCE TO RELATED APPLICATIONS

This Application is a U.S. national stage entry under 35 USC § 371 of Patent Cooperation Treaty Application PCT/EP2017/061090, filed May 9, 2017, which claims priority from U.S. Provisional Patent Application 62/335,885, filed May 13, 2016, both of which are incorporated herein by reference in their entireties.

FIELD

The present invention relates to balloon catheters for the invasive treatment of a body. The catheter comprises an elongate cooling element arranged centrally within a balloon to provide even cooling across the surface of the balloon.

BACKGROUND

From the late 1970s, catheters for cryotherapy have been used in the cardiovascular system starting from, for example, 1977 when it was used to surgically treat cardiac arrhythmias. Over the ensuing years it became widely recognised that cryotherapy was particularly advantageous for working in the heart. Its safety and efficacy was unsurpassed as surgeons were able to ablate delicate cardiac structures such as the A-V node, pulmonary veins and delicate perinodal atrial tissue without concern for thrombosis, perforation or other adverse events.

A catheter for the treatment of plaque stabilisation by cryotherapy is described in WO 2015/067414 (referred to hereinafter as WO'414). A balloon is inflated around a catheter shaft and subsequently cooled. A co-axially arranged cooling element is used to achieve this, wherein a liquid coolant is conveyed from an inner supply lumen into a larger conduit. When exiting the supply lumen the coolant undergoes a phase change due to the pressure drop which occurs, causing it to evaporate and reduce in temperature. The cold gas is then removed using a return lumen which surrounds the supply lumen in a co-axial manner.

A number of advantages are provided by the above co-axial design, as discussed in WO'414. For example, a single layered balloon may be used since there is little risk of a gas coolant leaking from the catheter. Furthermore cooling occurs, via the phase change, in the location where it is required without the need for insulating layers to be provided. Further still, the cooling element and its supporting lumen may maintain a small cross sectional area, making it suitable for applications in small diameter arteries, for example for the treatment of coronary vascular diseases. There remains a need however to improve known designs of catheters for cryotherapy.

SUMMARY OF THE INVENTION

According to an aspect of the invention, there is provided a catheter comprising: a flexible heat transfer element provided on an outer surface of the catheter; a conduit arranged to supply an inflation fluid for inflating the flexible heat transfer element so as to form an inflated balloon; a guide wire lumen for receiving a guide wire; and an elongate cooling element arranged to cool said inflation fluid for inflating the balloon; wherein said cooling element and said guide wire lumen are arranged inside the flexible heat transfer element such that, when inflated the cooling element is substantially central within the balloon and said guide wire lumen is parallel to and radially offset from the cooling element.

Preferably, said cooling element is arranged within the balloon so that, in use, the inner surface of the balloon is cooled substantially uniformly by the cooling element around the circumference of the balloon.

Preferably, the elongate cooling element extends along a longitudinal axis in a direction parallel to a central axis of the balloon.

Preferably, the central axis of the balloon is radially offset from the longitudinal axis of the elongate cooling element by 0.1 to 0.5 mm, more preferably 0.2 to 0.4 mm.

Preferably, the cooling element is arranged inside the flexible heat transfer element such that, when viewed in the plane normal to the longitudinal axis of the cooling element, the cooling element is provided substantially within the centre of the balloon.

Preferably, the flexible heat transfer member is configured to inflate anisotropically when viewed in the plane normal to the longitudinal axis of the cooling element so as to form the balloon.

Preferably, the flexible heat transfer element is configured to inflate into a substantially cylindrical balloon having first and second asymmetric ends.

Preferably, the conduit arranged to supply an inflation fluid, the guide wire lumen and the elongate cooling element are provided inside a shaft, wherein the flexible heat transfer element is adhered to the shaft at the first end, and wherein the flexible heat transfer element is adhered to the guide wire lumen at the second end.

Preferably, said cooling element comprises a first tube provided inside a second tube, wherein the first tube is substantially parallel to the second tube; and the second tube is configured to receive a flow of a coolant for cooling the cooling element from the first tube.

Preferably, in use, the first tube and the second tube are operated such that the pressure of the second tube is lower than the first tube.

Preferably, said cooling element comprises an elongate cooling chamber configured to receive coolant from the first tube and provide said coolant to the second tube.

Preferably, the elongate cooling chamber is arranged co-linearly with an end of the second tube.

Preferably, said cooling element further comprises a restriction tube configured to convey the coolant from the first tube to the cooling chamber, wherein said restriction tube has narrower internal diameter than the first tube.

Preferably, the restriction tube and cooling chamber are configured such that when the coolant conveyed along the first tube as a liquid, at least some of the coolant undergoes a phase change in the restriction tube and/or in the cooling chamber and returns through the second tube as a gas.

Preferably, said balloon is substantially cylindrical.

Preferably, in use in a vessel, the inflated flexible heat transfer element occludes fluid flow between the walls of the vessel and the inflated flexible heat transfer element.

Preferably, the conduit is further configured to provide a return flow of the inflation fluid of the flexible heat transfer element.

Preferably, the conduit comprises: a third tube for providing a supply flow of the inflation fluid of the flexible heat transfer element; and a fourth tube for providing a return flow of the inflation fluid of the flexible heat transfer element.

Preferably, said cooling element is not attached to the end of the guide wire lumen and wherein said cooling element is configured such that, when in use, the flow of the coolant causes the cooling element to vibrate.

Preferably, the flexible heat transfer element has single walled outer membrane.

Preferably the catheter further comprises a heater for heating the inflation fluid, or solidified inflation fluid, of the flexible heat transfer element.

Preferably, the conduit, the guide wire lumen and the cooling element protrude from a shaft, wherein, inside the shaft, the cooling element has an outer surface having a flattened-circular shape when viewed in the plane normal to the longitudinal axis of the cooling element.

Preferably the conduit, the guide wire lumen and the cooling element protrude from a shaft, the shaft comprising a solid body occupying the regions between the conduit, the guide wire lumen and the cooling element.

LIST OF FIGURES

Embodiments of the invention will now be discussed with reference to the accompanying drawings in which.

DESCRIPTION OF EMBODIMENTS

Figure 1:
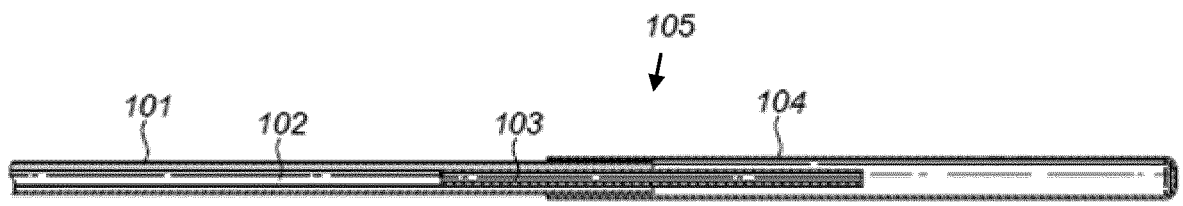
FIG. 1 is a schematic illustration of a cross section of a cooling element of a catheter according to an embodiment.

There is a motivation in known balloon catheters, in particular that of WO'414, to position the guide wire lumen (OWL) centrally within the shaft and the balloon to ease the insertion of the catheter into a body, and simplify the manufacturing process. Since the GWL is centrally disposed within the balloon, the cooling element must be provided off-centre, as viewed in a plane normal to the longitudinal axis of the cooling element. Due to the thermal resistance of the fluid which is inside the balloon when the balloon is inflated, areas of the surface of the balloon which are further from the cooling tube will not be cooled as quickly or effectively as those which are nearer the cooling tube. The surface of the balloon and any surrounding tissue will therefore cool unevenly.

Embodiments of the invention provide a new and advantageous design of balloon catheter. The new design of catheter overcomes the above problem of uneven cooling by arranging the cooling element and the GWL inside the flexible heat transfer element, such that, when inflated, the cooling element is substantially central within the balloon and the GWL is parallel to and radially offset from the cooling element. Spatial variations in heat transfer across the balloon are hence reduced, thereby enabling improved cryotherapy. Further still, the advantages of the cooling elements disclosed in WO'414 may be retained.

The catheter design has a wide range of applications, particularly in the field of coronary vascular diseases, which may include plaque stabilisation. Of course, the size of the catheter may be adjusted depending on the application and thus the catheter is also in principle suitable for other applications including atrial fibrillation, the treatment of renal denervation and tumour ablation.

The catheter is a balloon catheter and comprises a plurality of lumens supported inside a common shaft, except for in a balloon region where they are instead provided within a flexible heat transfer element. The flexible heat transfer element is configured to be inflated to form a balloon. One or more lumens are provided inside the shaft for providing a supply and return of inflation fluid to the balloon, as well as the cooling element for cooling the inflation fluid. The cooling element extends from the shaft and is preferably unsupported within the balloon but embodiments also include the cooling element being attached to the GWL.

The cooling element is elongate and typically substantially cylindrical, comprising tubular walls. The cooling element also preferably comprises first and second tubes for providing supply and return paths of a coolant, wherein the first tube (which is also referred to herein as the supply lumen) is provided inside a larger second tube (which is also referred to herein as the return lumen). The first tube and the second tube are each elongate and extend along axes that are substantially parallel to one another. The distal tip of the return lumen may be closed, whereas the distal tip of the supply lumen may be open and stop short of the end of the return lumen such that coolant may flow from the supply lumen in a first direction into the return lumen, and then flow in a second direction, opposite to the first direction, back along the return lumen. When the coolant flows from the supply lumen to the return lumen it moves into a region of increased volume and consequently reduces in pressure. This causes a phase change in the coolant, wherein at least some of the coolant will evaporate, causing the temperature of the cooling element to reduce.

The one or more lumens that provide supply and return flows of a fluid for inflating the balloon are preferably completely separate from the lumens used to supply the coolant. The inflation of the balloon and the cooling of the cooling element are preferably performed by separate mechanisms and these operations can be controlled and operated independently of each other.

The catheter may also contain a means for heating the inflation fluid within the balloon. This could be used, for example, if the inflation fluid froze during treatment and it was necessary to rapidly thaw the inflation fluid. The ability to induce such rapid thawing is particularly beneficial in case the catheter needs to be removed from an artery quickly, for example in emergency situations. The heat could be provided by any type of heater, for example a small electric heater, such as a resistor, positioned inside the balloon but outside the cooling element and supplied by an electric current via wires running down the catheter shaft. The heater element could be formed by a thin film resistor printed on the outer surface of the cooling element, a discrete resistor positioned inside the balloon, or by the inflation fluid itself. In the case where the inflation fluid forms the heater element, wires would supply electricity to electrodes at the proximal and distal ends of the balloon and terminate there, in contact with the inflation fluid, so that an AC or DC current could be passed through the inflation fluid inside the balloon, causing it to warm up.

In use, the catheter is inserted into a body such that the balloon region is positioned next to a region of tissue to be cooled in a vessel. For example, if the catheter is used instead for plaque stabilisation by cryotherapy, the balloon region may be positioned next to the plaque. The catheter's balloon is inflated by a liquid and the outer surface of the balloon comes into thermal contact with the tissue. Coolant is supplied to the cooling element and the temperature of the cooling element reduces. The inflation liquid within the balloon contacts the outer surface of the cooling element and is thereby cooled. It is important to remove all gas from the balloon prior to inflating, as gas bubbles in the balloon will have an impact on the heat conduction through the balloon. This is typically performed using a vacuum pump or syringe before the catheter is inserted into the body. However it may alternatively be performed in vivo.

An advantageous aspect of the above-described catheter design is that the coolant of the cooling element is not the same as the fluid used to inflate the balloon. The cooling element can safely support a phase change of the coolant since the cooling element is closed. Since the coolant is not in fluid communication with the inflatable flexible heat transfer membrane, there is little chance of it leaking from the catheter into a blood vessel and so the requirement to have a double layered balloon may be avoided. A single layered balloon is significantly more maneuverable and streamlined than a balloon with multiple membranes. Moreover, the catheter design is simpler than known designs employing a double balloon system and this reduces costs and manufacturing complexity.

The arrangement of the coolant supply lumen inside the coolant return lumen allows for the cooling element to maintain a small cross sectional area. This, in combination with the fact that only one cooling element is required, enables the catheter (in particular the shaft) to maintain a small diameter. This makes it particularly suitable for applications in small diameter arteries, such as in the coronary or smaller peripheral vasculature, where known catheter designs are difficult to insert and/or manoeuvre.

A further benefit of the preferred cooling element design is that cooling due to the phase change occurs in a clearly defined location that can be controlled as required. This improves the efficiency of the catheter system since the lumens that deliver coolant do not need to have high levels of insulation between the coolant and the surrounding environment. Moreover, the parallel arrangement of supply and return lumens means that the liquid coolant is kept cool by the cold, gaseous coolant returning from the distal tip of the catheter. This helps prevent the liquid coolant from boiling as it flows into that part of the catheter which is inside the body (and therefore at 37° C.).

The cooling element and the guide wire lumen are arranged inside the flexible heat transfer element such that, when inflated the cooling element is substantially central within the balloon and the guide wire lumen is parallel to and radially offset from the cooling element. The central axis of the balloon will typically extend through the elongate cooling element, in the direction of the longitudinal axis of the cooling element. In embodiments where the balloon is elongate, for example, substantially cylindrical, the central axis of the balloon is also the major axis of the balloon.

The longitudinal axis of the cooling element is generally not exactly the same as the central axis of the balloon. It is advantageous to arrange the cooling element so that the thermal resistance between the cooling element and the surface of the balloon is uniform in all radial directions (i.e. all directions perpendicular to the longitudinal axis of the cooling element). In order to compensate for the presence of the GWL (and any other lumen that may be provided inside the balloon), this may mean that the cooling tube is not exactly centred inside the balloon. The cooling element is therefore only 'substantially central' within the balloon. In some embodiments the longitudinal axis of the cooling element may be distally offset from the central axis of the balloon by anything from 0 to 33% of the radius of the balloon, more typically 0 to 20%. For example, for a cylindrical 3 mm diameter balloon having a 1 mm diameter cooling element, the centre of the cooling element may be up to 0.5 mm offset from the centre of the balloon, as viewed in a plane normal to the longitudinal axis of the cooling element. The exact position of the cooling element within the balloon may vary slightly during use as the cooling element may be free to vibrate inside the balloon. However the arrangement of the cooling element relative to the GWL should remain the same.

Further advantages of embodiments are set out in the detailed description provided below.

FIG. 1 shows a cross section of the design of a cooling element 105 of a catheter according to an embodiment. On the left hand side of FIG. 1 are shown the tubular supply lumen 102 and the tubular return lumen 101 of the coolant. The supply lumen 102 is positioned inside the return lumen 101 in a substantially co-axial configuration. An end of the supply lumen 102 is connected to, and in fluid communication with, a restriction tube 103. The restriction tube 103 has a narrower diameter than the supply lumen 102. The other end of the return lumen 101 to that connected to the supply lumen 102 ends in a cylindrical cooling chamber 104 of cooling element 105. In the present embodiment, the cooling chamber 104 has a slightly larger diameter than the return lumen 101 and extends over the outside of the return lumen 101.

In use, a flow of pressurised coolant is input to the supply lumen 102. The coolant may be a liquid or a mixture of a liquid and a gaseous form of the coolant. The restriction tube 103 at the end of the supply lumen 102 ensures that there is little pressure drop within the supply lumen 102 and so most, or all, of the pressurised liquid coolant remains in the liquid phase in the supply lumen 102. Along the length of the restriction tube 103, the pressure drops from a maximum value at the connection to the supply lumen 102 to a lower pressure at the exit of the restriction tube 103 into the cooling chamber 104. When the liquid coolant flows into the restriction tube 103 the pressure drop caused by the restriction means that the pressure of the liquid falls below its vapour pressure at the temperature of its surroundings at that point. This causes at least some of the liquid coolant to evaporate and undergo a phase change into a gas. Liquid coolant that flows from the restriction tube 103 into the cooling chamber 104 will also expand and may evaporate within the cooling chamber 104 and/or return lumen 101. The expansion of the coolant, and the phase change of the coolant, has a cooling effect on the walls of the cooling chamber 104. The coolant then flows from the cooling chamber 104, in liquid and/or gaseous form, through the return lumen 101. The pressure within the return lumen 101, and thereby the cooling chamber 104, is preferably reduced by a vacuum pump. The vacuum pump, described in more detail later, operates on the other end of the return lumen 101 to that connected to the cooling element 105. The reduction of pressure both increases the cooling effect due to expansion and phase change of the coolant and ensures that the coolant in the cooling chamber 104 flows into the return lumen 101.

Figure 2:
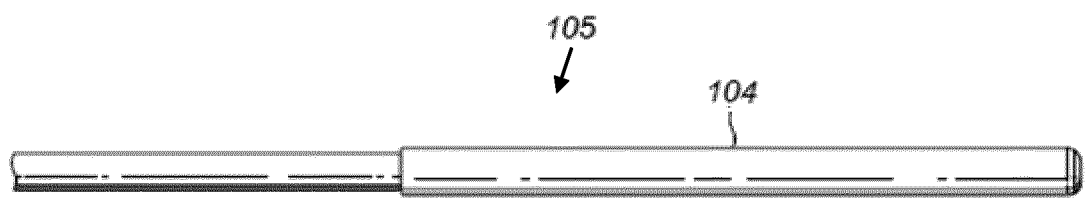
FIG. 2 is a schematic illustration of a cooling element of a catheter according to an embodiment.

FIG. 2 shows a perspective of the cooling element 105 of FIG. 1. The cooling chamber 104 has a slightly larger diameter than the return lumen 101. A greater cooling effect is achieved since more coolant will undergo a phase change in the cooling chamber 104. In addition, the outer diameter of the cooling chamber 104 has a larger surface area and is therefore more effective at cooling the inflation fluid.

Preferably the lumens of the cooling element are made of reasonably strong materials so that they can withstand the pressure of a pressurised coolant. In some embodiments these lumens also have a degree of flexibility so that the catheter can deform to match the profile of an artery.

The supply lumen 102, return lumen 101 and restriction tube 103 may be made of nylon, tri-layered tubing, polyimide, PEBAX™, such as PEBAX 55D, or other suitable materials. The supply lumen 102 and return lumen 101 may also be metal or polymer braided to add extra strength and flexible properties. The restriction tube 103 and supply lumen 102 may be made at the same time so that they are integral with each other, or they may be constructed as separate components and then glued together. Furthermore the cooling chamber 104 may be made entirely, or in part, of copper so that the cooling chamber 104 has good thermal conductivity properties. Alternatively, the entirety of the cooling element 105 may be made from polyimide, as this material is strong, enabling the walls to be made extremely thin. Using the same material throughout the cooling element 105 also improves the ease of manufacture of said cooling element.

Preferably, the coolant is $N_2O$ and enters the restriction tube 103 with substantially all of the coolant being in the liquid phase. The coolant may exit the restriction tube 103 with some of the $N_2O$ being in the liquid phase and some of the $N_2O$ being in the gas phase. Preferably, most of the $N_2O$ is in the liquid phase.

Figure 3:
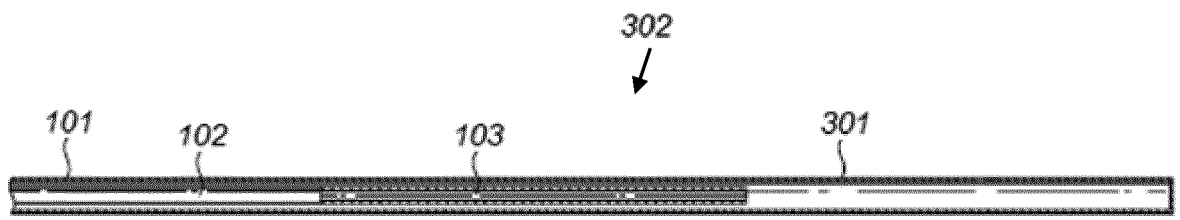
FIG. 3 is a schematic illustration of a cross section of a cooling element of a catheter according to an embodiment.

The embodiment shown in FIG. 3 differs from that shown in FIG. 1 in that the cooling chamber 301 of the cooling element 302 has the same inner and outer diameters as the return lumen 101. The cooling chamber 301 is still closed, i.e. blocked, at the other end to that connected to the return lumen 101. The dimensions and materials of the return lumen 101, supply lumen 102 and restriction tube 103 may be the same as described above with reference to FIGS. 1 and 2. The length of the cooling chamber 301 from the end of the restriction tube 103 to the closed end of the cooling chamber 301 is preferably 1 mm to 15 mm. Advantageously, the cooling chamber 301 is narrower than that shown in FIGS. 1 and 2.

The presence of a restriction tube 103 and a distinct cooling chamber 104 is optional however. In alternative embodiments, the liquid coolant may flow directly from the supply lumen 102, into the return lumen 101, either through the distal tip (i.e. end) of the supply lumen 102 or through one or more apertures in the wall of supply lumen 102, distributed along its length. In this case, some of the coolant may undergo a phase change when moving to enter the return lumen 101, which has a lower pressure than the supply lumen 102. This lower pressure may be achieved by ensuring that the annular internal volume of the return lumen 101 is larger than the internal volume of the supply lumen 102 and/or by using a vacuum pump.

Figure 4:
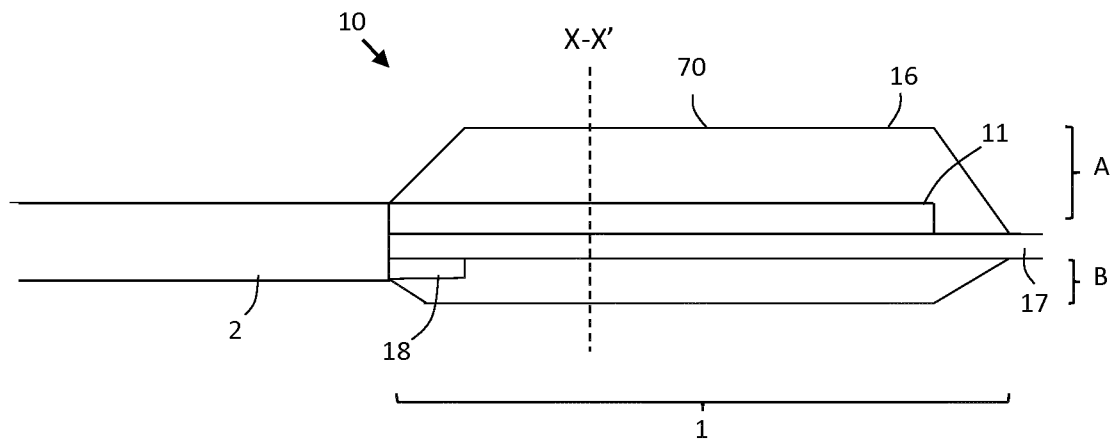
FIG. 4 is a schematic illustration of the distal end of a catheter according to an embodiment.

FIG. 4 is a perspective view of a catheter 10 according to an embodiment. The catheter 10 comprises a hollow tubular shaft 2 which extends along the length of the catheter and envelops the lumens provided within except in a balloon region 1, where an inflatable flexible heat transfer member 16 is provided. The shaft 2 is made of polyether block amide as braided, or unbraided, PEBAX™, such as PEBAX 55D, and is formed using extrusion or a heat reflow process.

The interior of the shaft 2 comprises a conduit 18, an elongate, cylindrical cooling element 11 and a cylindrical guide wire lumen (GWL) 17. The cooling element 11 may be similar to any of the embodiments described in FIGS. 1 to 3 and comprises a supply lumen 102 provided inside a return lumen 101.

The cooling element is provided within an inflatable heat transfer element in the form of a membrane 16 that is configured to be inflated into a balloon 70. The cooling element extends along the longitudinal axis of the balloon 16 in a straight line until it terminates near the distal end of the balloon, preferably approximately midway along the distal half of the balloon region 1. The cooling element 11 is centrally arranged and the flexible heat transfer member 16 shaped such that, when the balloon 70 is inflated, a substantially even cooling distribution is applied across the balloon 70. In particular the cooling element 11 and the guide wire lumen (GWL) are arranged such that the outside of the balloon 70 (i.e. the surface of the inflatable heat transfer membrane 16) is cooled quickly and uniformly. This is later discussed in more detail in connection with FIG. 5.

The GWL 17 is configured to be threaded over a surgically implanted guide wire 15 (shown in FIG. 5), when in use, for positioning the catheter 10 inside a patient. The GWL 17 extends from the guide wire entrance aperture at the distal tip of the catheter 10, to a guide wire exit aperture provided on the shaft 2 (as is standard for Rapid Exchange catheters). Alternatively, an 'over the wire' configuration may be used. The GWL 17 is a hollow tube and is made of tri-layer or a similar material.

The inflatable heat transfer membrane 16 is adhered to the distal tip of the shaft 2 on its proximal end and the GWL 17 on its distal end. The central region between these two ends is configured to be inflated into a substantially elongate, and substantially cylindrical balloon 70. Although the schematic illustration of FIG. 4 shows the membrane 16 to extend from the shaft 2 at the proximal end of the balloon region 1 at a sharp, constant angle up towards a cylindrical region (and back from this region towards the GWL 17 at the distal end), it should be understood that this profile is typically tapered, with the shape being primarily dictated by the elasticity and shape of the flexible heat transfer membrane 16, rather than any internal supporting members. The angle at which the membrane 16 extends from the shaft 2 at the proximal end of the balloon region 1 and later adjoins onto to the GWL 17 at the distal end of the balloon region 1 varies about the longitudinal axis 60 of the cooling element 11 (and the central axis 50 of the balloon). This ensures that the cooling element 11 is located centrally within the balloon 70, as is evident by FIG. 4. This means that although the central region of the balloon 70 is substantially uniform and cylindrical, the tapered end regions are asymmetric.

Embodiments also include the inflated balloon alternatively being substantially spherical. A degree of asymmetry may be introduced however in order to achieve central positioning of the cooling element inside the balloon. The conduit 18 (referred to herein as the inflation lumen) is provided for supplying an inflation fluid for inflating the flexible heat transfer membrane 16 so as to form the inflated balloon 70. The inflation lumen 18 extends along the inside of the shaft 2 and, in this embodiment, protrudes from the shaft 2 into the balloon region 1. Alternatively however the inflation lumen may terminate at the end of the shaft 2. In some embodiments a plurality of said inflation lumens may be provided in order to allow faster inflation or to reduce the overall cross sectional area of the shaft 4 since in some instance two or more small inflation lumens may be physically easier to accommodate inside the shaft 2 than one large inflation lumen.

The shaft 2, and in particular, the space between the lumens provided inside the shaft 2, may act as a return path for providing a flow of inflation fluid from the balloon 70 back along the shaft 2 in a reverse direction to the flow of inflation fluid in the inflation lumen 18. This enables space savings inside the shaft 2 since it is not necessary to provide a separate deflation tube. Alternatively, the flow direction of the inflation fluid may be reversed such that the conduit 18 behaves as a deflation lumen whilst the shaft 2 behaves as an inflation lumen. Furthermore the shaft 2 and/or inflation lumen 18 may function as both an inflation and deflation lumen in some circumstances, in which case the pressure is simply reversed at one end of the shaft 2 and/or inflation lumen 18.

It is desirable to provide a shaft 2 having a small diameter so as to allow the catheter to more readily fit through small vessels. In an embodiment this may be achieved using a process called 'reflow' where the outer wall of the shaft 2 is extruded around the inner lumens of the shaft 2 (comprising the inflation lumen 18, GWL, the cooling element 11 and optionally a separate deflation lumen), so as to form a solid body completely filling the space between the inner lumens and the outside surface thereby joining the inner lumens together. This composite construction allows for a reduced thickness of the wall of the reflowed shaft beyond what it would be if the shaft were provided in the form of a separate tube surrounding the inner lumens. Typically this reduction is equivalent to the thickness of the outer tube of a shaft 5, which may be between 0.1-0.3 mm.

In an alternative embodiment the overall diameter of the shaft 2 may be reduced by providing a cooling element 11 having an outer surface in the form of a flattened circle, such as an oval or an ellipse, as viewed in a plane normal to the longitudinal axis of the cooling element 11, across the shaft 2. In this case, the remaining lumens which extend along the inside of the shaft 2 may be arranged around the smaller outer diameter of the cooling element 11. This enables a shaft 2 in the form of a tube having a smaller diameter than would otherwise be possible to be used to tightly surround the inner lumens. The return lumen 101 of the cooling element 11 may be formed so as to maintain its flattened-circular shape section along its length (including the portion protruding from the shaft 2). Alternatively the return lumen 101 may be formed of a compliant material which deforms inside the shaft 2 so as to form the flattened-circular inside the shaft, whilst maintaining a circular cross-section outside of the shaft 2.

In an embodiment, the cooling element 11 is attached to the GWL 17 inside the balloon region 1. However, in a preferred embodiment, the cooling element 11 is not attached to the GWL 17 inside the balloon region 1 and so the cooling chamber is free to vibrate, i.e. move laterally with respect to the longitudinal axis of the GWL 17.

The closed distal end of the return lumen may typically extend approximately an additional 2.0 to 3.0 mm from the open distal end of the supply lumen. This region could be thought of as the cooling chamber 104.

The following dimensions may be desirable for certain applications that may include the treatment of plaque stabilization and atrial fibrillation on a human or animal:

Cooling element 11
  Outer diameter=0.35 to 1.0 mm
  Outer wall thickness=0.019 to 0.05 mm
  Length=15 to 30 mm
Return lumen 101
  Outer diameter=0.35 to 1.0 mm
  Outer wall thickness=0.019 to 0.05 mm
  Length=1000 to 1750 mm
Supply lumen 102
  Outer diameter=0.12 to 0.4 mm
  Outer wall thickness=0.014 to 0.05 mm
  Length=1000 to 1750 mm
Restriction tube 103
  Outer diameter=0.0762 to 0.140 mm
  Outer wall thickness=0.019 to 0.0254 mm
  Length=5 to 50.8 mm
Inflation lumen 18
  Outer diameter=0.254 to 0.406 mm
  Outer wall thickness=0.0191 to 0.0508 mm
  Length=1000 to 1750 mm
GWL 17
  Outer diameter=0.40 to 1.0 mm
  Inner diameter=0.35 to 0.95 mm
  Length=650 mm
Shaft 2
  Diameter=1.35 to 3.3 mm Embodiments also include other dimensions, in particular the dimensions as provided in WO'414 which are incorporated herein by reference, and the above dimensions may be scaled up or down so that the catheter can be used with vessels of any size.

The cooling element is encompassed by the balloon 70. That is to say, in use the cooling element 11 is within the inflation fluid of the balloon 70 and there is no membrane of the balloon 70 arranged between the inflation fluid and the cooling element 11.

The balloon 70 is typically 15 mm to 30 mm long and, when deflated, is preferably substantially flush with the outer surface of the shaft 2 so that the outer diameter of the catheter is not increased by the deflated balloon. For example, the outer diameter of the catheter may be substantially 4 Fr (i.e. 1.333 mm). When inflated, the outer diameter of the balloon 70 may be 2.5 mm to 4 mm. A larger balloon 70 may be required in the treatment of atrial fibrillation however with a diameter of approximately 24 mm (e.g. +/−10%). The dimensions of the catheter components, such as the lumen, may be adjusted depending on the application and, in particular, the size which the balloon is configured to be inflated. For example, larger lumen may be desired in order to inflate and deflate a large balloon more quickly, or apply an increased cooling effect.

The balloon 70 may be made of a variety of materials and is desirably compliant or semi-compliant to ensure a good fit with the target area for effective heat exchange and a more even temperature distribution around the tissue. The balloon 70 may also be non-compliant if this is appropriate for the desired application. The balloon design and construction may be as known in the art of balloon angioplasty. However, there is no need for the balloons to be as strong, and with as thick membranes, as those used for angioplasty since the inflation pressures used in embodiments are substantially lower than those used in angioplasty. This is because the balloons are not required to enlarge the vessel. The balloons in embodiments are only required to make a good thermal contact with the vessel and the balloons are therefore preferably made with a thinner membrane than balloons used for angioplasty. The balloons can be made of a variety of materials such as silicone or polyurethane for compliant balloons and nylon or polyester for non-complaint balloons. Wall thickness will also vary depending on the properties to be achieved and are generally in the range of 5 to 100 microns. The balloon may also have a substantially smooth exterior surface so that heat transfer is optimised from the tissue on the interior surface of the vessel. The balloon material and thickness may be optimised to minimize thermal losses through the balloon wall.

Figure 5:
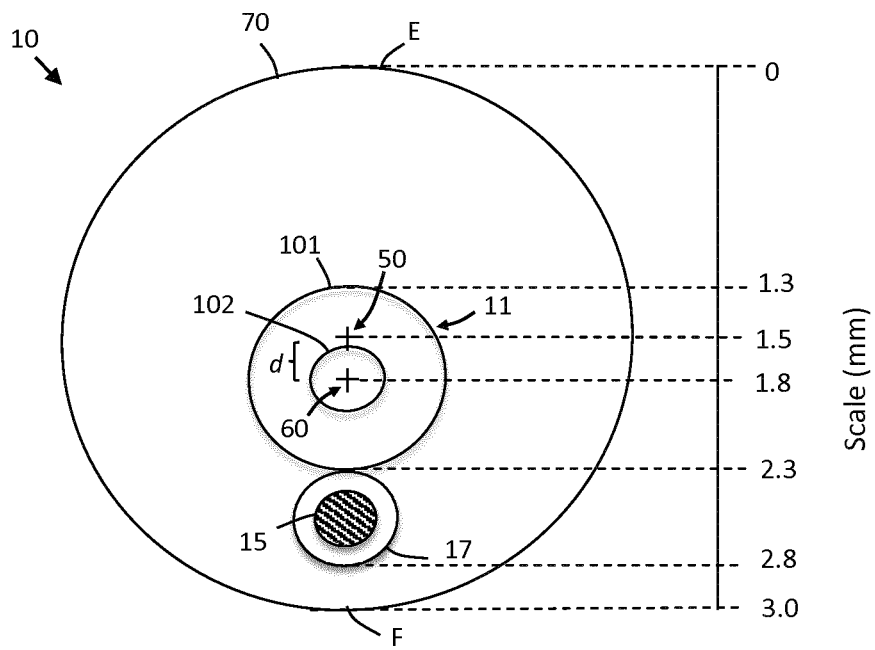
FIG. 5 is a schematic illustration of a cross section of the distal end of a catheter according to an embodiment.

The balloon 70 may also be formed from a membrane 16 which is shaped, stretched or otherwise configured such that the balloon 70 inflates anisotropically (i.e. asymmetrically) when viewed in the plane normal to the longitudinal axis of the cooling element. In other words, the balloon 70 may radially expand from the GWL 17 onto which it is secured by different amounts so as to ensure that the cooling element 11 is substantially central within the balloon 70. An example of this is shown in FIG. 4 where the region A of the balloon 70 that extends between the GWL 17 and an upper surface E of the balloon 70 is greater than the region B which extends between the GWL 17 and a lower surface F of the balloon 70. In the embodiment of FIGS. 4 and 5 the range A extends 2.3 mm radially, whereas distance B extends 0.2 mm radially, as is evident from the scale on FIG. 5.

In use, an inflation fluid is supplied to the inflation lumen 18 to inflate the balloon 70. The cooling element 11 is then cooled by the expansion and/or evaporation of the coolant as described in the above embodiments. The flow of the coolant that may be a liquid and/or gas, from the supply lumen 102 to the return lumen 101 (potentially via a restriction lumen and cooling chamber, if provided) causes the distal end of the cooling element, if it is not fixed to the GWL 17, to vibrate. Advantageously, this vibration movement of the cooling element 105 increases the agitation of the inflation fluid and thereby the flow over and around the cooling chambers 104 and thereby both increases the rate at which the inflation fluid is cooled and the temperature uniformity of the inflation fluid. The inflation fluid is in contact with the inner surface of the balloon 70 and the balloon 70 is thereby cooled as the inflation fluid is cooled. The outer surface of the balloon 70 is therefore cooled due to the cooling of the inflation fluid by the cooling element. When an operator determines that sufficient cooling has been applied by the catheter, the balloon 70 is deflated using the deflation lumen and the catheter can then be removed.

The catheter could alternatively be realised with the cooling element 11 being fixed to the GWL 17. However, this will help maintain the relative position of the cooling element to the balloon. The vibration of the balloon may be reduced from if the cooling element was not fixed to the GWL, but the vibration is preferably not entirely prevented.

Preferably the inflation fluid has a fixed volume. This limits any damage caused by any leakage of the inflation fluid from the catheter. Any leakage of the inflation fluid can also be detected by monitoring the pressure of the inflation fluid when the balloon 70 is inflated or by determining if the amount of inflation fluid after a procedure is the same as that at the start of the procedure.

The inflation fluid is preferably a liquid so that even if there is a leakage from the catheter, the leakage is of a liquid and not a gas. The inflation fluid may be a solution that comprises sodium chloride, such as saline, with a sodium chloride concentration of about 0.9%, or a solution with a higher concentration of sodium chloride, preferably a 25% concentration of sodium chloride. The inflation fluid is preferably water based, and may include various additives to lower the freezing point. Additives may include one or more of sodium chloride, calcium chloride, ammonia, ethanol, propylene glycol, ethylene glycol, propanone and butanone. Other additives may also be used, including contrast media. The inflation fluid is also preferably sterile. To ensure that the inflation fluid is sterile, the inflation fluid may be provided from a separate container, such as a pre-packed bag or syringe that is connected to the catheter.

The same apparatus for supplying the inflation fluid to into the inflation lumen 18 may have its operation reversed so that it is also able to deflate the balloon 70 by removing the inflation fluid. For example the inflation fluid may be injected into the lumen 18 by an operator pressing on the plunger of a syringe. The same syringe can also be used to remove the inflation fluid by the operator withdrawing the plunger. Advantageously, such an arrangement allows an operator to easily determine if any of the inflation fluid has leaked from the catheter by checking for entrained air bubbles or blood in the inflation circuit following plunger withdrawal.

FIG. 5 is a cross-sectional view of the catheter of FIG. 4 taken through the X-X' plane. The arrangement of the cooling element 11 and the GWL 17 relative to the central (i.e. 'longitudinal' or 'major') axis 50 of the balloon 70 is schematically illustrated. The cooling element 11 comprises a supply lumen 102 co-axially arranged inside a return lumen 101, as previously described. The cooling element 11 extends along its longitudinal axis 60 in a direction parallel to the central axis 50 of the balloon 70. The longitudinal axis 60 is displaced from the central axis 50 by a distance d in a radial direction (perpendicular to axes 50 and 60). The cooling element 11 is still arranged substantially centrally within the balloon 70 however, with the central axis 50 of the balloon 70 extending through the cooling element 11. In this case the central axis 50 extends through the annular region between the supply lumen 101 and the return lumen 102. In other embodiments the central axis 50 of the balloon 70 may extend through the supply lumen 101. The longitudinal axis 60 is typically radially offset from the central axis 50 by less than 0.5 mm, more typically between 0.1 to 0.4 mm.

The distance of separation d between the central axis 50 of the balloon 70 and the longitudinal axis 60 of the cooling element 11 is chosen such that, when the cooling element 11 cools the surrounding inflation fluid, the increased thermal resistance of the GWL 17 relative to the inflation fluid is compensated for such that the surface of the balloon 70 is cooled uniformly (including, the opposing edges E and F).

The GWL 17 is provided substantially off-centre with respect to the balloon 70 such that the central axis 50 does not extend through the GWL. The outside of the GWL 17 is typically radially offset from the central axis 50 by at least 0.5 mm, more preferably 0.5 to 1.8 mm.

A scale is also shown in FIG. 5 to illustrate an example of a possible arrangement in accordance with an embodiment. The scale runs from opposing edges E and F of the balloon 70. In this embodiment a 3 mm diameter inflated balloon 70 encases a cooling element 11 having a 0.4 mm diameter supply lumen 102 provided inside a 1.0 mm diameter return lumen 101. Also provided is a 0.5 mm diameter GWL 17. As shown, the return lumen 101 extends 1.3 mm to 2.3 mm from edge E and has its longitudinal axis 60 at a distance 1.8 mm from the edge of the balloon 70. The balloon has a radius of 1.5 mm and so the distance d between the central axis 50 of the balloon 70 and the longitudinal axis 60 of the cooling element 11 in this case is 0.3 mm. In other embodiments this separation may be between 0.1 to 0.5 mm, more preferably 0.2 to 0.4 mm.

As viewed in FIG. 5, the GWL 17 extends approximately 2.3 mm to 2.8 mm from the edge E such that it is in contact with the outside of the cooling element 11. An inflation fluid surrounds the outside of the cooling element 11 and the GWL 17, filling the remaining volume shown inside the balloon 70, including in the region 2.8 mm to 3.0 mm between the outside of the GWL 17 and the balloon 70. In alternative embodiments the GWL 17 may be at least partially in contact with the flexible heat transfer membrane 16 which forms the surface of the balloon 70, however preferably the GWL 17 is not attached to the membrane 16.

Figure 6:
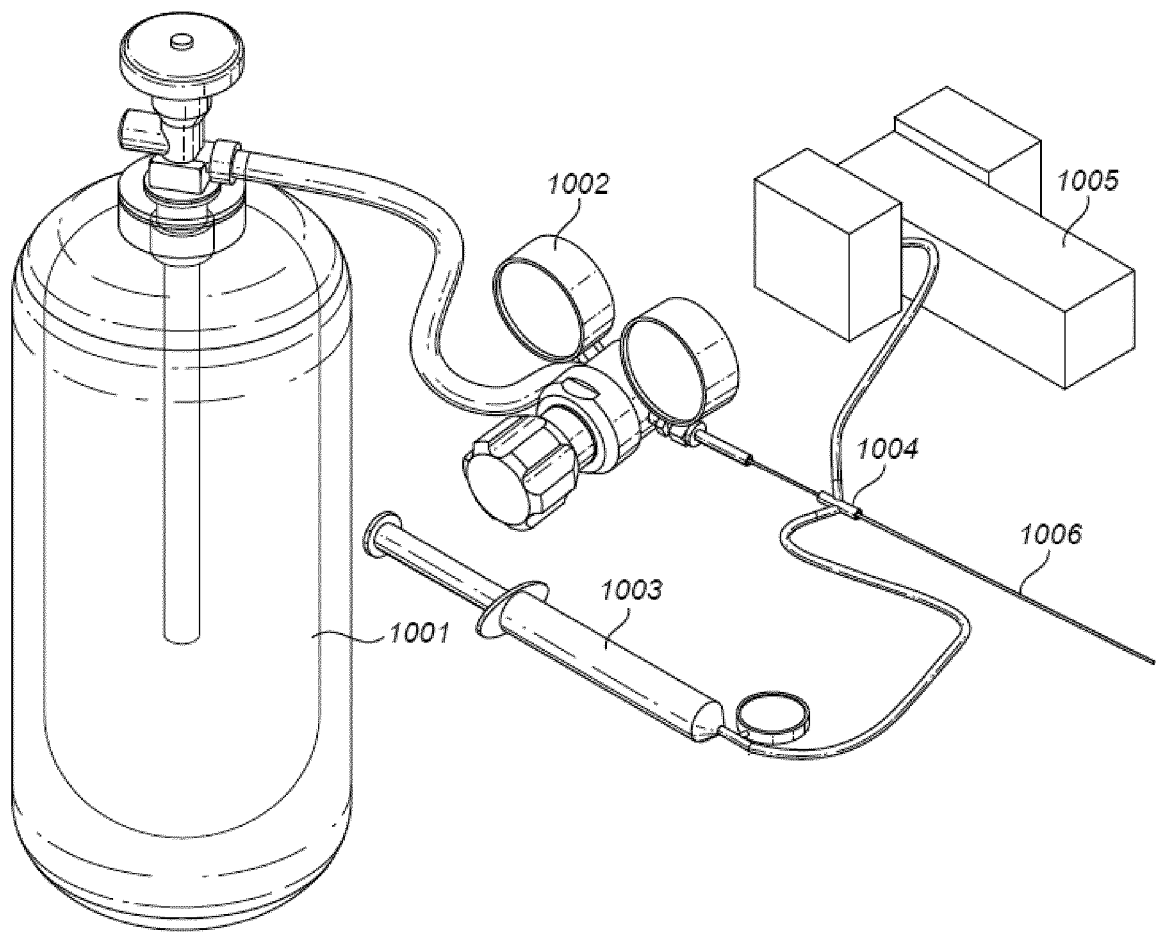
FIG. 6 is an illustration of a system for operating a catheter according to an embodiment.

FIG. 6 is an illustration of an exemplary system for using the catheter according to the embodiments described herein to cool a target part of a vessel. It will be understood that some of the specifically described components may not be essential to the operation of the system but are described for context only. Suitable, functionally similar, or equivalent components may be used interchangeably.

The system comprises:
Coolant cylinder 1001
Pressure regulator 1002
Tri-connector 1004
Vacuum pump 1005
Inflation device 1003
Catheter shaft 1006

Although not shown in FIG. 6, the system also comprises a catheter end according to any of the embodiments described herein.

The coolant cylinder 1001 has a dip tube and spigot valve for controlling the supply of the coolant. A flexible high pressure hose connects the coolant cylinder to the pressure regulator 1002. An injection tube from the pressure regulator connects to the tri-connector 1004. Also connected to the tri-connector is an inflation tube connected to inflation device 1003 and a vacuum tube connected to the vacuum pump 1005. The tri-connector maintains the injection tube, the vacuum tube and the inflation tube as separate from each other. The tri-connector also connects to the catheter shaft 1006 and thereby supports fluid and/or gas communication between the catheter and the coolant supply, vacuum pump, and inflation device.

The system may also include a heat exchanger, not shown in FIG. 6, to cool the liquid coolant before it enters the catheter. This will prevent boiling of the coolant as it enters the warm environment of the patient's body. Heat may be removed from the liquid coolant by using a refrigeration circuit or Peltier cooler.

The system may further comprise a computer, such that the system may be software controlled, the computer having one or more controls and/or a user interface such as a graphical user interface. The system may also further include assemblies for temperature and/or pressure monitoring based on signals received from one or more sensors.

The inflation device 1003 operates by causing an inflation fluid to flow into the catheter shaft 1006 when the plunger is pressed. The inflation device is also a deflation device since the inflation fluid flows back into the device from the catheter when the plunger is withdrawn. The inflation device may alternatively be an electric pump.

The vacuum pump 1005, that may be an electric vacuum pump, operates on the return lumens of the coolant. The vacuum pump 1005 advantageously lowers the pressure in the return lumen and/or cooling chamber of the cooling elements to thereby increase the amount of phase change of the coolant that occurs. The vacuum pump 1005 also ensures that the coolant in the supply lumens and cooling chambers (where provided) flows into the return lumen.

A further advantage applying the vacuum pump 1005 to the return lumens is that the pressure in the return lumen is relatively low and less than typical blood pressure in a body. In use, should the return lumens leak, this would result in blood flowing into the return lumens rather than the coolant flowing out. The vacuum pump 1005 thereby improves the safety of the catheter.

The system may also comprise a deflation device, separate from the inflation device 1003, that is in fluid communication with the catheter shaft 1006 through an additional separate connection to the tri-connector. The deflation device may be a vacuum pump, such as an electric vacuum pump.

Variables that influence the operation of the catheter are the pressure of the inflated balloon and the temperature of the outer surface of the balloon. Both of these are controllable by how the system of FIG. 6 is operated. The pressure of the balloon is controllable by controlling the amount, and pressure of, the inflation fluid by inflation device 1003. The temperature of the outer surface of the balloon is dependent on both the temperature of the cooling element, and how long the cooling element has been cooling the inflation fluid. The temperature of the cooling element is controllable by controlling the pressure and the amount of coolant that flows into the catheter. The length of time that the inflation fluid is cooled by the cooling element is easily controlled by when the system operator starts and stops the flow of the coolant into the catheter.

Preferably, the pressure of the balloon is maintained at lower than 5 ATM (507 kPa), typically between 3.5 ATM (355 kPa) to 4.5 ATM (456 kPA), but may be as low as 3 ATM (304 kPa) or 1 ATM (101 kPa). It may be desirable for the balloon pressure to be as low as possible for effective treatment in order to mitigate the risk of a reaction occurring in the blood vessel that leads to re-stenosis or blockage. A short-term response to the application of high-pressure cryotherapy is also often smooth muscle cell proliferation, which is potentially dangerous. The tissue interface temperature is preferably maintained within a desired range in order to remove heat from the plaque and vessel without significantly ablating the cells. It is noted that throughout the present document, all pressures given as gauge pressures, that is, above atmospheric pressure.

The temperature of the outer surface of the balloon is maintained within appropriate ranges given the application. For example, for cryotherapy, the temperature is preferably maintained between +15° C. (288K) and −35° C. (238K) and more preferably between 0 to −30° C. (273K to 243K). For atrial fibrillation (and other applications where tissue ablation is required) the temperature may be much lower, for example between −50° C. to −90° C. (223K to 183K), although typically around −80° C. (193K).

The exact temperature will depend on the treatment application, according to standard practice. Depending on the type of balloon and the heat load, there may be a temperature difference of about 10° C. to 40° C. between inner and outer balloon temperature and this can be compensated for when controlling the system.

Preferably, sensors are provided within, on or near the catheter end, such as on or just inside the balloon, in order to monitor and thereby control the temperatures and pressures in a feedback control system. For example, a thermocouple may be fixed to the GWL or coolant return tube to measure the temperature inside the balloon. One or more further thermocouples may be attached to the internal or external surface of the balloon in order to measure the balloon tissue interface temperature. In addition, a pressure sensor may be placed inside the balloon to accurately monitor and thereby control the pressure within the balloon. The pressure sensor may be an open hydraulic tube with no flow, or may be positioned on the inflation circuit near the inflator, so that the fluid pressure inside the tube is measured outside the catheter. The pressure sensor may also be a piezoelectric transducer, fibre-optic transducer or other type of sensor. Pressure sensors and a flow meter may also be positioned in the coolant circuit, to measure the pressure and flow of the coolant.

Both temperature and pressure signals can be used to control refrigerant flow such that balloon pressure and/or surface temperature remain within the desired ranges. The pressure transducer may also be used to detect any leaks within the catheter by sensing abnormal pressures. The temperature sensor(s) may also be used to detect vessel occlusion by the balloon.

As described earlier, the catheter may also comprise means for heating the inflation fluid, or solidified inflation fluid, within the balloon. Advantageously, this allows frozen inflation fluid to be thawed quickly if required.

In order to support the sensors, means for heating and any other devices at the distal end of the catheter, the system may further comprise connectors to one or more power supplies, data interfaces, or other signal processing units, configured to provide a power supply, control signals and to convert sensor signals into data. Electrical wires may be housed in the catheter shaft together with the lumens or along the outside of the catheter shaft.

Preferably, the volume of the inflation fluid is fixed and small. This minimises the damage caused by any leakage. The injection of the inflation fluid to inflate the balloon may be automatically controlled and performed, for example, by an operator pressing a button. Alternatively, the inflation fluid may be injected manually.

According to known techniques, one or more portions of the catheter may be radiopaque and/or include a radiopaque marker. This aids the operator of the catheter.

The cooling elements are typically characterised by supply lumen provided inside a return lumen. The supply lumen may be positioned centrally within the return lumen but this is not essential. The supply lumen may alternatively lie along a side of the return lumen or be in no way fixed to the return lumen so that its position within the return lumen can change.

Further embodiments of the invention include those in which the elongate cooling element is also the guide wire lumen. For example, the cooling element itself may be configured to receive a guide wire such that a separate guide wire lumen is not required. In embodiments wherein the cooling element comprises a return lumen provided inside a supply lumen, either the supply or the return lumen may be arranged to receive a guide wire. This provides the advantage of simplifying the design, thereby enabling the overall size of the shaft to be reduced, as well as offering more structural support.

Further embodiments include a number of modifications and variations that can be made to the embodiments as described above. In particular, all of the dimensions provided in the figures are approximate and embodiments include catheter designs with different dimensions. Furthermore the dimensions may also vary depending on the size of the human or animal that is being treated. Throughout the present document various features are described as lumens and tubes. These terms may be used interchangeably and said features may also be referred to as conduits.

In the above described embodiments the cooling element is preferably substantially straight and co-linear with the abutting end of the shaft. The cooling element may be rigid and non-flexible. However, the cooling element is preferably flexible so that it can bend, as is appropriate if the balloon is positioned in a curved section of artery.

In the above-described operation of the system, operational temperatures and pressures are provided. However, embodiments are in no way limited to these operational temperatures and pressures. Moreover, the operational temperatures and pressures may be varied depending on the application. In particular, embodiments include the catheter, and the system supporting the catheter, being operated according to the disclosure in WO 2012/140439 A1, the entire contents of which are incorporated herein by reference.

The balloons according to embodiments may have a thinner membrane than balloons used for angioplasty. However, embodiments also include using balloons with the same thickness as those used in angioplasty so that the balloons advantageously act as a secondary barrier in case of a leak in the cooling tube.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims.

The invention claimed is:

1. A catheter comprising:
   a flexible heat transfer element provided on an outer surface of the catheter;
   a conduit arranged to supply an inflation fluid for inflating the flexible heat transfer element so as to form an inflated balloon;
   a guide wire lumen for receiving a guide wire; and
   an elongate cooling element arranged to cool said inflation fluid for inflating the balloon;
   wherein said cooling element and said guide wire lumen are arranged inside the flexible heat transfer element such that, when inflated the cooling element is substantially central within the balloon and said guide wire lumen is parallel to and radially offset from the cooling element; and
   wherein the flexible heat transfer member is configured to inflate anisotropically when viewed in the plane normal to the longitudinal axis of the cooling element so as to form the balloon.

2. The catheter according to claim 1, wherein said cooling element is arranged within the balloon so that, in use, the inner surface of the balloon is cooled substantially uniformly by the cooling element around the circumference of the balloon.

3. The catheter according to claim 1, wherein the elongate cooling element extends along a longitudinal axis in a direction parallel to a central axis of the balloon.

4. The catheter according to claim 3, wherein the central axis of the balloon is radially offset from the longitudinal axis of the elongate cooling element by 0.1 to 0.5 mm, more preferably 0.2 to 0.4 mm.

5. The catheter according to claim 1, wherein the cooling element is arranged inside the flexible heat transfer element such that, when viewed in the plane normal to the longitudinal axis of the cooling element, the cooling element is provided substantially within the centre of the balloon.

6. The catheter according to claim 1, wherein the flexible heat transfer element is configured to inflate into a substantially cylindrical balloon having first and second asymmetric ends.

7. The catheter according to claim 1, wherein the conduit arranged to supply an inflation fluid, the guide wire lumen and the elongate cooling element are provided inside a shaft, wherein the flexible heat transfer element is adhered to the shaft at the first end, and wherein the flexible heat transfer element is adhered to the guide wire lumen at the second end.

8. The catheter according to claim 1, wherein said cooling element comprises a first tube provided inside a second tube, wherein the first tube is substantially parallel to the second tube; and the second tube is configured to receive a flow of a coolant for cooling the cooling element from the first tube.

9. The catheter according to claim 1, wherein, in use, the first tube and the second tube are operated such that the pressure of the second tube is lower than the pressure of the first tube.

10. The catheter according to claim 9, wherein the elongate cooling chamber is arranged co-linearly with an end of the second tube, wherein said cooling element further comprises a restriction tube configured to convey the coolant from the first tube to the cooling chamber, wherein said restriction tube has narrower internal diameter than the first tube, and wherein the restriction tube and cooling chamber are configured such that when the coolant conveyed along the first tube as a liquid, at least some of the coolant undergoes a phase change in the restriction tube and/or in the cooling chamber and returns through the second tube as a gas.

11. The catheter according to claim 1, wherein said cooling element comprises an elongate cooling chamber configured to receive coolant from the first tube and provide said coolant to the second tube.

12. The catheter according to claim 1, wherein, said balloon is substantially cylindrical.

13. The catheter according to claim 1 wherein, in use in a vessel, the inflated flexible heat transfer element occludes fluid flow between the walls of the vessel and the inflated flexible heat transfer element.

14. The catheter according to claim 1, wherein the conduit is further configured to provide a return flow of the inflation fluid of the flexible heat transfer element.

15. The catheter according to claim 1, wherein the central axis of the balloon extends through the elongate cooling element, in the direction of the longitudinal axis of the cooling element.

16. The catheter according to claim 1, wherein said cooling element is not attached to the end of the guide wire lumen and wherein said cooling element is configured such that, when in use, the flow of the coolant causes the cooling element to vibrate.

17. The catheter according to claim 1, wherein the flexible heat transfer element has single walled outer membrane.

18. The catheter according to claim 1, further comprising a heater for heating the inflation fluid, or solidified inflation fluid, of the flexible heat transfer element.

19. The catheter according to claim 1, wherein the conduit, the guide wire lumen and the cooling element protrude from a shaft, and wherein, inside the shaft, the cooling element has an outer surface having a flattened-circular shape when viewed in the plane normal to the longitudinal axis of the cooling element.

20. The catheter according to claim 1, wherein the conduit, the guide wire lumen and the cooling element protrude from a shaft, the shaft comprising a solid body occupying the regions between the conduit, the guide wire lumen and the cooling element.

* * * * *